(12) United States Patent
Tanabe et al.

(10) Patent No.: US 6,861,551 B2
(45) Date of Patent: Mar. 1, 2005

(54) PROCESSES FOR THE PREPARATION OF MACROCYCLIC KETONES

(75) Inventors: Yoo Tanabe, Nishinomiya (JP); Atsushi Makita, Toda (JP)

(73) Assignee: Japan Energy Corporation, Tokyo (JP)

( * ) Notice: Subject to any disclaimer, the term of this patent is extended or adjusted under 35 U.S.C. 154(b) by 17 days.

(21) Appl. No.: 10/239,078

(22) PCT Filed: Mar. 28, 2001

(86) PCT No.: PCT/JP01/02583

§ 371 (c)(1),
(2), (4) Date: Sep. 19, 2002

(87) PCT Pub. No.: WO01/74752

PCT Pub. Date: Oct. 11, 2001

(65) Prior Publication Data

US 2003/0078455 A1 Apr. 24, 2003

(30) Foreign Application Priority Data

Apr. 4, 2000 (JP) ......................... 2000-101905

(51) Int. Cl.$^7$ ............................................... C07C 69/74
(52) U.S. Cl. ......................... 560/126; 568/346; 568/354
(58) Field of Search ........................... 560/126; 568/346, 568/354

(56) References Cited

U.S. PATENT DOCUMENTS 4,335,261 A    6/1982   Ueda

OTHER PUBLICATIONS

R. Hamasaki, et al.: Koryo, Terupen Oyobi Seiyu Kagaku Ni Kansura Toronkai, Koen Yoshishu, vol. 44 (XP001091208), pp. 382–384 (Sep. 1, 2000).
Yoshihiro Yoshida et al., Catalytic TMSCl Promoted Powerful Aldol Addition and Claisen Condensation Mediated by TiCl$_4$/Bu$_s$N Agent: Comparison and Evaluation with the Mukaiyama Aldol Addition, Tetrahedron Letters 40 (1999) pp. 4227–4230.
Yuen–May Choo et al., Synthesis of Civetone from Palm Oil Products, JAOCS, vol. 71, No. 8, (1994) pp. 911–913.
Philip Jones et al., Oxidative Radical–Mediated Transannulation Reactions Directed Towards Polycycle, Synlett (1997), vol. 4, pp. 398–400.
Yoo Tanabe et al., Dichloro–Bis (Trifluoromethanesulfonato) Titanium (IV) As An Effective Promoter In the Claisen Ester Condensation, Chemistry Letters (1984), pp. 1867–1870.
Yoo Tanabe et l., Power ful Claisen Condensation and Claisen–Aldol Tandem Reaction of α, α–dialkylated Esters Promoted by ZrCl$_4$–Pr$_2$Net, Chem. Commun.,(2001), pp. 1674–1675.
Yoshihiro Yoshida et al., TiCl$_4$/Bu3N/(catalytic TMSOTf): Efficient Agent for Direct Aldol Addition and Claisen Condensation, Tetrahedron Letters (1997), vol. 38, No. 50, pp. 8727–8730.
Yoo Tanabe et al., Mild, Effective and Selective Method for the Silylation of Alcohols Using Silazanes Promoted by Catalytic Tetrabutylammonium Fluoride, Tetrahedron Letters (1994), vol. 35, No. 45, pp. 8409–8412.
Yoo Tanabe et al., A Facile Synthesis of 1,3–Dicarbonyl Compounds From 1–Alkyne and Acid Anhydride Promoted by Dichloro–Bis (Trifluoromethanesulfonato) Titanium (IV), Chemistry Letters (1985), pp. 673–676.
Yoo Tanabe et al., The Crossed Claisen Ester Condensation Mediated by Titanium (IV) Bistriflate, Chemistry Letters (1986), pp. 1813–1816.
Yoo Tanabe et al., The Selective Claisen and Dieckmann Ester Condensations Promoted by Dichlorobis(trifluoromethanesulfonato) titanium (IV), Bull. Chem. Soc. Jpn. (1989), 62, pp. 1917–1924.
Yoo Tanabe et al., Carbon Homologation of 1–Alkynes Using Alkoxymethyl Esters Mediated by Dichlorobis(trifluoromethanesulfonato) titanium (IV), Bull. Chem. Soc. Jpn., 67, (1994), pp. 3309–3313.
Ryota Hamasaki et al., A Highly Efficient Synthesis of Civetone, Tetrahedron 56 (2000), pp. 7423–7425.
Yoo Tanabe et al., Practical Synthesis of (Z)–Civetone Utilizing Ti–Dieckmann Condensation, Adv. Synth. Catal. 2002, vol. 344, No. 5, pp. 507–510.

*Primary Examiner*—Paul J. Killos
(74) *Attorney, Agent, or Firm*—Sughrue Mion, PLLC

(57) ABSTRACT

Disclosed are a process of subjecting a diester of a long-chain dicarboxylic acid having 18 to 21 carbon atoms to intramolecular condensation in the presence of titanium tetrachloride or zirconium tetrachloride and a trialkylamine to form an α-alkoxycarbonylated macrocyclic ketone, and a process for producing a macrocyclic ketone by hydrolyzing an α-alkoxycarbonylated macrocyclic ketone obtained by the process and then subjecting the hydrolyzate to decarboxylation. The invention provides a process for producing a macrocyclic ketone efficiently, which permits high concentration synthesis.

3 Claims, No Drawings

PROCESSES FOR THE PREPARATION OF MACROCYCLIC KETONES

This application is a 371 of PCT/JP01/02583 Mar. 28, 2001.

TECHNICAL FIELD

The present invention relates to a process for producing macrocyclic ketones to be utilized as products such as fragrances and intermediates thereof in high efficiency.

BACKGROUND OF THE INVENTION

Macrocyclic ketones, e.g., civetone represented by the following general formula (1), are known as fragrant ingredients of musk, and are sold at very high prices.

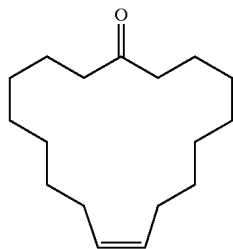

(1)

A large number of reports have been made on the processes for producing civetone (a recent review: Alvin S. Williams, Synthesis, 1999, 10, 1707–1723). For example, known is a process of using a diester of 9-octadecenedioic acid produced by metathesis of an ester of oleic acid as an starting material, forming an α-alkoxycarbonylated macrocyclic ketone by Dieckmann condensation and an α-carboxy macrocyclic ketone by hydrolysis, and then subjecting the α-carboxy macrocyclic ketone to decarboxylation (Choo, Yuen et al., J. Am. Oil Chem. Soc. 1994, 71(8), 911–913).

By the way, in so-called Claisen condensation wherein esters having α-hydrogen are condensed in the presence of a strong base to form a β-ketoester, Dieckmann condensation used in the above process is particularly called by that name when two esters involved in the reaction are present in the same molecule and an α-alkoxycarbonylated macrocyclic ketone is formed. In general, Dieckmann condensation is advantageous to the formation of 5-, 6-, or 7-membered ring.

In the case of forming a 13-membered or larger ring by Dieckmann condensation, because the probability of an intermolecular reaction of esters becomes higher than that of an intramolecular reaction of esters when the esters are reacted at a usual concentration, the ring closure is carried out according to a high dilution process (Advanced Organic Chemistry, 4th ed., Jerry March, John Wiley & Sons, 1992, 491–493).

Accordingly, also in the above synthesis of civetone, the synthesis is carried out under a highly diluted condition of a concentration of 0.024 mol/L using a strong base of potassium hydride as a Dieckmann condensation reagent, and thus the reaction efficiency is very bad.

Recently, the present inventors have reported a novel process for Claisen condensation (Dieckmann condensation) using titanium tetrachloride ($TiCl_4$), tributylamine ($Bu_3N$) and, if necessary, chlorotrimethylsilane (TMSCl) catalyst (Y. Tanabe et al., Tetrahedron Letters 1999, 40, 4227–4230). According to the process, α-carbomethoxycyclopentanone having a 5-membered ring can be obtained in 95% yield by reacting dimethyl ester of hexanedioic acid in dichloromethane at −78° C. for 2 hours in the presence of $TiCl_4$, $Bu_3N$, and TMSCl catalyst.

As a result of the intensive studies on the process for Dieckmann condensation newly found, the inventors have found that, also in the ring formation of a diester of a long-chain dicarboxylic acid having 18 or more carbon atoms, surprisingly, an intramolecular reaction of esters proceeds predominantly over an intermolecular reaction of esters even when the reaction is carried out not according to a high dilution process but at a usual concentration.

The invention aims at solving the above problem, and an object of the invention is to provide a process for producing a macrocyclic ketone efficiently, which permits high concentration synthesis.

DISCLOSURE OF THE INVENTION

The process for producing a macrocyclic ketone according to the invention comprises a process of subjecting a diester of a long-chain dicarboxylic acid having 18 to 21 carbon atoms to intramolecular condensation in the presence of titanium tetrachloride or zirconium tetrachloride and a trialkylamine, particularly preferably subjecting the diester to intramolecular condensation by adding a mixed solution of the diester of the long-chain dicarboxylic acid having 18 to 21 carbon atoms and the trialkylamine and a solution containing titanium tetrachloride or zirconium tetrachloride into a reaction vessel at the same time, to form an α-alkoxycarbonylated macrocyclic ketone; and a process of hydrolyzing an α-alkoxycarbonylated macrocyclic ketone obtainable in the above process and then subjecting the hydrolyzate to decarboxylation.

BEST MODE FOR CARRYING OUT THE INVENTION

The diester of the long-chain dicarboxylic acid having 18 to 21 carbon atoms which is a starting material of the invention is represented by the following formula (2)

$$R_1O_2C\text{—}A\text{—}CO_2R_2 \quad (2)$$

and means a compound wherein the number of carbon atoms of the carboxylic acid containing the skeletal moiety A in the above formula is from 18 to 21.

The skeletal moiety A includes a linear or branched alkylene group and a divalent group wherein one or two or more of the bonds in the alkylene group are double bonds or triple bonds.

$R_1$ and $R_2$ in the above formula each may be any hydrocarbon group without any problem, and particularly preferred is a lower alkyl group having 1 to 4 carbon atoms such as methyl, ethyl, propyl, isopropyl, or butyl; benzyl group, or phenethyl group. Moreover, the $R_1$ and $R_2$ may be the same or different.

Particularly preferred specific examples of the diester of the long-chain dicarboxylic acid having 18 to 21 carbon atoms include dimethyl ester, diethyl ester, dipropyl ester, diisopropyl ester, dibutyl ester, dibenzyl ester, diphenethyl ester, and the like of octadecanedioic acid, nonadecanedioic acid, eicosanedioic acid, heneicosanedioic acid, octadecenedioic acid, nonadecenedioic acid, eicocenedioic acid, heneicocenedioic acid, and the like.

Moreover, the trialkylamine is preferably an amine of lower alkyl groups each having 1 to 4 carbon atoms, and particularly preferred is triethylamine ($Et_3N$) or $Bu_3N$.

For subjecting these diesters of the long-chain dicarboxylic acids as starting materials to intramolecular condensation, the following processes are particularly preferred.

(1) A process of continuously mixing a solvent-diluted solution of a diester of a long-chain dicarboxylic acid and a trialkylamine with $TiCl_4$ (or a solvent-diluted solution) or a suspension of zirconium tetrachloride ($ZrCl_4$) over a certain period of time.

(2) A process of incorporating a solvent-diluted solution of a diester of a long-chain dicarboxylic acid and a trialkylamine into a suspension of $ZrCl_4$ over a certain period of time.

(3) A process of continuously mixing a solvent-diluted solution of a diester of a long-chain dicarboxylic acid and a trialkylamine with $ZrCl_4$ portionwise.

The amount of the trialkylamine in this case is from 2 to 4 mol, preferably 2.5 to 3.5 mol per mol of the starting material, and the amount of $TiCl_4$ or $ZrCl_4$ is from 2 to 4 mol, preferably 2.5 to 3.5 mol per mol of the starting material.

Any solvent may be used as far as it is inert to the reaction, but preferred is a hydrocarbon, an aromatic hydrocarbon, or a halogenated hydrocarbon, and particularly preferred is dichloromethane or toluene.

When the amount of the solvent is too small, the intermolecular reaction tends to occur, which results in decrease of yield. On the other hand, when the amount is too large, there arise inconveniences that the reaction proceeds only slowly, the reaction efficiency per a certain volume becomes bad, and so forth. Therefore, the amount is suitably selected depending on the kind of the starting material, but in general, it is preferred to select the amount from such a range that the concentration of the starting material becomes from 0.08 to 0.2 mol/L.

With regard to the reaction temperature, the reaction is carried out at a temperature of −20 to 80° C., preferably −10 to 30° C. The reaction time may be suitably selected in consideration of the concentration of the reaction solution, mixing rate, and the like.

By the intramolecular condensation, an α-alkoxycarbonylated macrocyclic ketone, e.g., an α-alkoxycarbonylcivetone of the following formula (3) in the case that a diester of 9-octadecenedioic acid is used as a stating material, is formed.

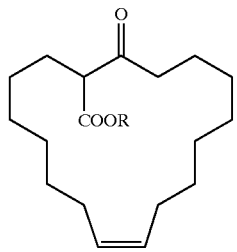

(3)

The α-alkoxycarbonylated macrocyclic ketone can be converted into a macrocyclic ketone by hydrolysis and decarboxylation according to the known method (e.g., Choo, Yuen et al., J. Am. Oil Chem. Soc. 1994, 71(8), 911–913).

By the way, the stereochemical configuration of 9-octadecenedioic acid obtainable by microbiological oxidation is, in principle, a cis-isomer. Since a cis→trans isomerization is considered not to occur in Dieckmann condensation, only cis-isomer of civetone is, in principle, obtained.

The following will explain the invention with reference to specific examples but the scope of the invention is not limited thereto.

EXAMPLE 1

2-Methoxycarbonyl-9-cycloheptadecenone

Under an argon stream, $CH_2Cl_2$ solvent (0.1 ml) was placed in a flask beforehand, and thereto were added dropwise, at 0 to 5° C., a mixed solution of dimethyl cis-9-octadecenedioate (141 mg, 0.41 mmol) and $Bu_3N$ (230 mg, 1.24 mmol) in $CH_2Cl_2$ (1.7 ml) and a solution of $TiCl_4$ (132 μl, 1.20 mmol) in $CH_2Cl_2$ (2.0 ml) at the same time over a period of 1 hour by means of a microfeeder. The whole was further mixed at the same temperature for 15 minutes. Water was added to the reaction mixture and the resulting mixture was stirred and then extracted with ether. The organic layer was washed with water and saturated brine, and then dried over anhydrous sodium sulfate. After the evaporation of the solvent under reduced pressure, the crude product was purified by silica gel chromatography (hexane/ethyl acetate=20/1→10/1) to obtain the aimed product (57 mg, 45%) and a by-product (34-membered ring; 22 mg, 17%).

Colorless Oil $^1$H-NMR (400 MHz, $CDCl_3$) δ: 1.18–1.44 (16H, m), 1.53–1.71 (2H, m), 1.75–1.87 (1H, m), 1.88–2.09 (5H, m), 2.52 (2H, t, J=6.8 Hz), 3.49 (0.93H, dd, J=9.0 Hz, J=5.4 Hz: keto form), 3.70 (2.78H, s: keto form), 3.75 (0.22H, s: enol form), 5.28–5.40 (2H, m), 12.72 (0.07H, s: enol form).

$^{13}$C-NMR (100 MHz, $CDCl_3$) δ: 23.34, 26.46, 26.58, 26.79, 27.05, 27.95, 27.99, 28.08, 28.15, 28.35, 28.45, 28.98, 29.01, 41.54, 52.24, 58.42, 130.07, 130.14, 170.22 (keto form), 175.51 (enol form), 206.34.

EXAMPLE 2

2-Methoxycarbonyl-9-cycloheptadecenone

Under an argon stream, $CH_2Cl_2$ solvent (0.5 ml) was placed in a two-necked flask beforehand, and thereto were added dropwise, at 0 to 5° C., a mixed solution of dimethyl cis-9-octadecenedioate (170 mg, 0.50 mmol) and $Bu_3N$ (278 mg, 1.50 mmol) in $CH_2Cl_2$ (2.1 ml) and a solution of $TiCl_4$ (159 μl, 1.45 mmol) in $CH_2Cl_2$ (2.5 ml) at the same time over a period of about 1 hour by means of a microfeeder. The whole was further mixed at the same temperature for 15 minutes. Water was added to the reaction mixture and the resulting mixture was stirred and then extracted with ether. The organic layer was washed with water and saturated brine, and then dried over anhydrous sodium sulfate. After the evaporation of the solvent under reduced pressure, the crude product was purified by silica gel chromatography (hexane/ethyl acetate=20/1→10/1) to obtain the aimed product (75 mg, 49%) and a by-product (34-membered ring; 26 mg, 18%).

EXAMPLE 3

2-Methoxycarbonyl-9-cycloheptadecenone

Under an argon stream, $CH_2Cl_2$ solvent (0.5 ml) was placed in a two-necked flask beforehand, and thereto were added dropwise, at 0 to 5° C., a mixed solution of dimethyl cis-9-octadecenedioate (170 mg, 0.50 mmol) and $Et_3N$ (152 mg, 1.50 mmol) in $CH_2Cl_2$ (2.15 ml) and a solution of $TiCl_4$ (159 μl 1.45 mmol) in $CH_2Cl_2$ (2.45 ml) at the same time over a period of about 1 hour by means of a microfeeder. The whole was further mixed at the same temperature for 15 minutes. Water was added to the reaction mixture and the resulting mixture was stirred and then extracted with ether. The organic layer was washed with water and saturated brine, and then dried over anhydrous sodium sulfate. After the evaporation of the solvent under reduced pressure, the crude product was purified by silica gel chromatography (hexane/ethyl acetate=20/1→10/1) to obtain the aimed product (83 mg, 54%) and a by-product (34-membered ring; 21 mg, 14%).

EXAMPLE 4

2-Methoxycarbonyl-9-cycloheptadecenone

The aimed product (54 mg, 35%) and a by-product (34-membered ring; 26 mg, 17%) were obtained in a similar manner to the method described in Example 3 ($TiCl_4/Et_3N$ system) using toluene as a solvent.

EXAMPLE 5

2-Methoxycarbonyl-9-cycloheptadecenone

Under an argon stream, to a suspension of $ZrCl_4$ (338 mg, 1.45 mmol) in $CH_2Cl_2$ (1.0 ml) were added dropwise, at 0 to 5° C., a mixed solution of dimethyl cis-9-octadecenedioate (170 mg, 0.50 mmol) and $Bu_3N$ (278 mg, 1.50 mmol) in $CH_2Cl_2$ (4.0 ml) over a period of about 1 hour by means of a microfeeder. The whole was further mixed at the same temperature for 15 minutes. Water was added to the reaction mixture and the resulting mixture was stirred and then extracted with ether. The organic layer was washed with water and saturated brine, and then dried over anhydrous sodium sulfate. After the evaporation of the solvent under reduced pressure, the crude product was purified by silica gel chromatography (hexane/ethyl acetate=20/1→10/1) to obtain the aimed product (43 mg, 28%) and a by-product (34-membered ring; 6 mg, 4%).

EXAMPLE 6

2-Methoxycarbonyl-9-cycloheptadecenone

Under an argon stream, $CH_2Cl_2$ solvent (0.5 ml) was placed in a two-necked flask beforehand, and thereto was added dropwise, at 0 to 5° C., a mixed solution of dimethyl cis-9-octadecenedioate (170 mg, 0.50 mmol) and $Bu_3N$ (278 mg, 1.50 mmol) in $CH_2Cl_2$ (4.5 ml) over a period of about 1 hour by means of a microfeeder. $ZrCl_4$ (338 mg, 1.45 mmol) was added portionwise every 10 minutes from 5 minutes after the start of dropwise addition of the above mixed solution, 6 times in total. After the completion of the dropwise addition of the mixed solution of the ester and the amine, the whole was further mixed at the same temperature for 15 minutes. Water was added to the reaction mixture and the resulting mixture was stirred and then extracted with ether. The organic layer was washed with water and saturated brine, and then dried over anhydrous sodium sulfate. After the evaporation of the solvent under reduced pressure, the crude product was purified by silica gel chromatography (hexane/ethyl acetate=20/1→10/1) to obtain the aimed product (28 mg, 18%) and a by-product (34-membered ring; 18 mg, 12%).

EXAMPLE 7

2-Methoxycarbonylcyclononadecanone

2-Methoxycarbonylcyclononadecanone (36 mg, 21%) and a by-product (38-membered ring; 29 mg, 17%) were obtained in a similar manner to the method described in Example 1 ($TiCl_4/Bu_3N$ system) using dimethyl eicosanedioate (185 mg, 0.50 mmol) as a substrate.
Colorless oil
1H-NMR (400 MHz, $CDCl_3$)δ:1.22–1.37 (28H, m), 1.52–1.72 (2H, m), 1.76–1.98 (2H, m), 2.46–2.61 (2H, m), 3.50 (0.96H, dd, J=8.5 Hz, J=6.1 Hz: keto form), 3.70 (2.87H, s: keto form), 3.75 (0.13H, s: enol form), 12.75 (0.04H, s: enol form).
$^{13}C$-NMR (100 MHz, $CDCl_3$)δ: 23.27, 26.86, 27.27, 27.44, 27.47, 27.57, 27.65, 27.83, 27.95, 28.15, 28.19, 28.22, 28.26, 28.53, 41.95, 52.25, 58.33, 170.28, 206.31.

EXAMPLE 8

9-Cycloheptadecenone (Civetone)

2-Methoxycarbonyl-9-cycloheptadecenone (92 mg, 0.30 mmol) was dissolved in a mixed solvent of 5% aqueous NaOH/ethanol/THF (2.5:5.0:2.5, vol./vol./vol.) and the solution was refluxed at 80° C. for 5 hours. After cooling to 0° C., the reaction solution was rendered slightly acidic using 10% sulfuric acid aqueous solution and the whole was further refluxed for 10 minutes. After the evaporation of the solvent under reduced pressure, the residue was extracted with ether. The organic layer was washed with saturated sodium hydrogen carbonate aqueous solution, water, and saturated brine, and then dried over anhydrous sodium sulfate. After the evaporation of the solvent under reduced pressure, the crude product was purified by silica gel chromatography (hexane/ethyl acetate=40/1) to obtain the aimed product (71 mg, 95%)
Colorless Oil With a Musky Odor
$^1H$-NMR (400 MHz, $CDCl_3$) δ: 1.24–1.39 (16H, m), 1.57–1.67 (4H, m), 1.96–2.06 (4H, m), 2.40 (4H, t, J=6.7 Hz), 5.30–5.39 (2H, m).
$^{13}C$-NMR (100 MHz, $CDCl_3$) δ: 23.84, 26.68, 28.11, 28.19, 28.58, 29.01, 42.41, 130.12, 212.50.

Since a diester of a long-chain dicarboxylic acid is subjected to intramolecular condensation in the presence of titanium tetrachloride or zirconium tetrachloride and a trialkylamine, the invention serves a particular effect that macrocyclic ketones can be synthesized at high concentration and thus can be produced efficiently.

INDUSTRIAL APPLICABILITY

As mentioned above, the process for producing macrocyclic ketones of the invention is suitable for producing products such as perfume and intermediates thereof efficiently.

What is claimed is:
1. A process for producing an α-alkoxycarbonylated macrocyclic ketone, which comprises subjecting a diester of a long-chain dicarboxylic acid having 18 to 21 carbon atoms to intramolecular condensation in the presence of titanium tetrachloride or zirconium tetrachloride and a trialkylamine.
2. The process for producing an α-alkoxycarbonylated macrocyclic ketone according to claim 1, wherein the intramolecular condensation is carried out by adding a mixed solution of the diester of the long-chain dicarboxylic acid having 18 to 21 carbon atoms and the trialkylamine and a solution containing titanium tetrachloride or zirconium tetrachloride into a reaction vessel at the same time.
3. A process for producing a macrocyclic ketone, which comprises hydrolyzing an α-alkoxycarbonylated macrocyclic ketone obtainable in the process according to the above claim 1 or 2 and subjecting the hydrolyzate to decarboxylation.

* * * * *